United States Patent [19]

Kondo et al.

[11] Patent Number: 5,094,950

[45] Date of Patent: Mar. 10, 1992

[54] DIETHYLENETRIAMINE PENTAACETIC ACID DERIVATIVES

[75] Inventors: Susumu Kondo; Miki Kurami; Makoto Azuma, all of Chiba, Japan

[73] Assignee: Nihon Medi-Physics Co., Ltd., Hyogo, Japan

[21] Appl. No.: 362,370

[22] Filed: Jun. 5, 1989

[30] Foreign Application Priority Data

Jun. 7, 1988 [JP] Japan ................ 63-139885
Jun. 7, 1988 [JP] Japan ................ 63-139886

[51] Int. Cl.⁵ .................. C07K 17/02; A61K 49/02
[52] U.S. Cl. .................. 530/391.5; 424/1.1; 424/9; 635/213; 635/215; 635/216; 635/217; 530/301; 530/303; 530/304; 530/306; 530/322; 530/345; 530/359; 530/362; 530/382; 530/408; 530/409; 435/188
[58] Field of Search .............. 530/390, 391, 303, 304, 530/306, 301, 359, 362, 382, 322, 345, 388, 408, 409, 405, 406; 424/1.1, 9; 435/215, 188, 216, 213, 217

[56] References Cited

U.S. PATENT DOCUMENTS

| | | | |
|---|---|---|---|
| 4,479,930 | 10/1984 | Hnatowich | 424/1.1 |
| 4,622,420 | 11/1986 | Meares et al. | 562/443 |
| 4,647,447 | 3/1987 | Gries et al. | 424/9 |
| 4,668,503 | 5/1987 | Hnatowich | 424/1.1 |
| 4,678,667 | 7/1987 | Meares et al. | 424/85.91 |
| 4,741,900 | 5/1988 | Alvarez et al. | 424/1.1 |
| 4,837,003 | 6/1989 | Nicolotti | 424/1.1 |
| 4,855,353 | 8/1989 | Kurami et al. | 525/54.1 |
| 4,867,973 | 9/1989 | Goers et al. | 424/85.91 |

FOREIGN PATENT DOCUMENTS 0173629 3/1986 European Pat. Off. .
0174853 3/1986 European Pat. Off. .
0233619 8/1987 European Pat. Off. .
0250358 12/1987 European Pat. Off. .

OTHER PUBLICATIONS

Essien et al., (1988) J. Med. Chem. 1988 31(5) 898-901.
Brechbiel et al., (1986) Inorg. Chem. 25:2772-2781.
Jung et al., (1981) Biochem. Biophys. Res. Commun. 101 (2):599-606.
Staros, J. V., Biochemistry 1982, 21, 3950-3955.
Haseman, M. K. et al., Eur. J. Nucl. Med. (1986) 12:455-460.
Otsuka, F. L. et al., Nucl Med. Biol. 14(3), 243-249 (1987).
Quadri, S. M. et al., Journal of Labelled Compounds and Radiopharmaceuticals vol. XXIII, Nos. 10-12, p. 1291, 1981.

Primary Examiner—Jeffrey E. Russel
Assistant Examiner—Kay Kim

[57] ABSTRACT

A compound of the formula II:

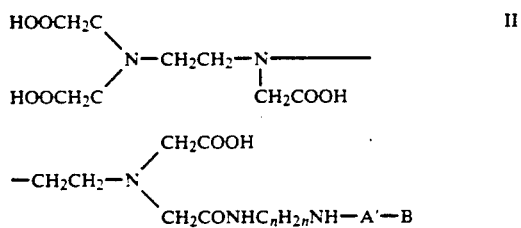

wherein n is an integer of 2 to 10,
A' is a bivalent linking group formed by reacting both the reactive groups of a cross linking reagent, and
B is a residue of a polypeptide compound, and physiologically acceptable salts thereof are disclosed. Such compound is useful as a non-radioactive carrier for radioactive metal elements.

15 Claims, No Drawings

DIETHYLENETRIAMINE PENTAACETIC ACID DERIVATIVES

BACKGROUND OF THE INVENTION

1. Field of the invention

The present invention relates to novel diethylenetriamine pentaacetic acid (hereinafter, referred to as DTPA) derivatives and radioactive metal complex thereof as well as application of the latter in the diagnostic and therapeutic fields.

2. Background information

Substances labeled with $^{131}$I have been widely used in nuclear medicine for the detection of specific diseases, pharmacokinetic research and therapy of specific diseases using radioisotope. These substances, however, have many deficiencies such as (a) relatively long half-life of radioactivity, (b) emission of useless beta-rays besides gamma-rays, (c) radiation exposure of tissues other than a targetted tissue due to in vivo deiodination of $^{131}$I and the like.

In view of said deficiencies, the use of other radioactive metal elements such as $^{111}$In and $^{99m}$Tc has been investigated as a substitute for $^{131}$I. These metal elements are usually used in a conjugated form with a carrier material comprising a ligand compound bonded to a physiologically active substance. In order to label physiologically active high molecular compounds such as fibrinogen, TPA (Tissue plasminogen activator), monoclonal antibodies and fragments thereof with radioisotopes (RI) as the metal elements, bifunctional chelating agents (BFC) have been widely utilized. Commonly used BFCs include anhydride (1) of DTPA, activated ester (2) thereof and ethylenediamine tetraacetic acid benzyl isothiocyanate (3).

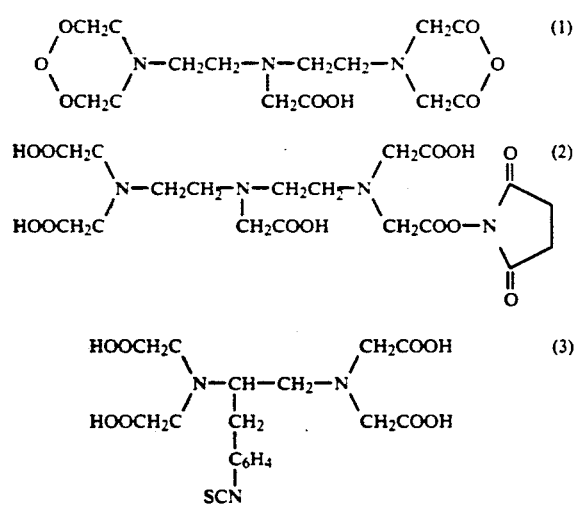

In all cases, these BFCs are bonded to the physiologically active substances by amide bonding (—NHCO—). This means that the available and hence selectable bonding site is limited to amino groups. This also means that when the active site of the particular physiologically active substance contains lysine residue, a serious consequence such as loss of the physiological activity may occur. In addition, grave problems, high uptake and long retention of RI in normal liver cells, may occur when amide bonding is applied for labeling a monoclonal antibody with RI. The cause of this problem is entirely attributed to the fact that the bonding between BFCs and physiologically active substances is limited to amide bonding. More particularly, monoclonal antibodies are destined to be metabolized in normal liver cells. In this process RIs may dissociate from BFC-antibodies before the enzymatic cleavage of BFC-RI from the antibodies because of greater strength of the amide bond and retained as hydrolysates in liver cells. Since, however, BFC-RIs are water soluble complexes, even if they are cleaved from biologically active substances, they are secreted into the blood stream and then excreted through the kidney, thus raising no problem. Therefore, it has been found necessary to develop BFCs which can provide various bonding modes not limited to the amide bond.

On the other hand, the bonding modes between the biologically active substance and BFC-RI have also importance in obtaining better quality of diagnosis or therapeutic effect. For example, TPA has a very short activity half-life of only a few minutes in the blood stream. Therefore, when RI-labelled TPA is adopted for diagnosing blood clot, an RI having correspondingly shorter half-life such as $^{99m}$Tc ($T_{1/2}$: 6 hours) should be selected, but $^{99m}$Tc has a rather long half-life. Since the target tissue for TPA-BFC-RI is the vascular blood clot to which the administered TPA-BFC-RI binds when contacted, if inactivation of TPA in said TPA-BFC-RI precedes decay of RI, the inactivated-TPA-BFC-RI remains in the blood stream. This will adversely affect the quality of diagnosis. Therefore, a bonding mode which allows rapid cleavage of BFC-RI from inactivated TPA and hence rapid excretion is desirable. While an unstable bond is preferred to a stable bond in the above example, there may be other examples in which the above relation is reversed. For instance, in the diagnostic agent for imaging tumors containing lesser vascularity, it is essential or at least desirable that a certain amount of RI necessary for diagnosis contacts and binds to the tumor lesion and accumulate.

In these cases, relatively stable bonding modes are preferred. Of course, when the tumor to be diagnosed or treated contains much vascularity, stable bonding modes are not preferred. Accordingly, there is a strong and continuous need for development of BFC which allows wide selection of bonding mode.

There has been proposed an alternative approach, different from the use of above-mentioned BFCs (1), (2) and (3), in which a carrier is prepared by forming Schiff base of DTPA-mono-(2-aminoethyl)amide with oxidized inulin (aldehydic inulin), followed by reduction (J. Med. Chem. 31, 898-901, 1988). In this approach, however, the bonding modes of inulin are limited and therefore this approach is not satisfactory.

The DTPA-$^{111}$In complex has been used as a radioactive diagnostic agent. Aromatic amide derivative, i.e. 2-aminoethylanilide of DTPA was described in J. Labelled Comp. Radiopharm., 23, 1291 (1981).

SUMMARY OF THE INVENTION

In the first aspect, the present invention provides a compound of the formula I:

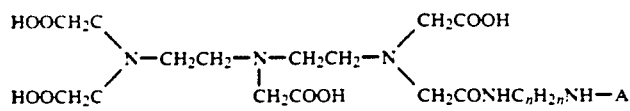

wherein n is an integer of 2 to 10, and

A is a monovalent group formed by reacting one of the two reactive groups of a cross linking reagent, and physiologically acceptable salts thereof. Such compound is useful as BFC for preparing a non-radioactive carrier for radioactive metal elements.

In the second aspect, the present invention provides a compound of the formula II:

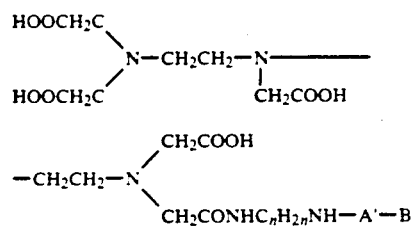

wherein n is an integer of 2 to 10,

A' is a bivalent linking group formed by reacting both the reactive groups of a cross linking reagent, and B is a residue of a polypeptide compound, and physiologically acceptable salts thereof. Such compound is useful as a non-radioactive carrier for radioactive metal elements.

In the third aspect, the present invention provides a carrier for radioisotopes comprising at least one compound of the formula II.

In the fourth and fifth aspects, the present invention provides a radioactive diagnostic agent comprising the compound of the formula II labeled with a radioactive metal element, and a radioactive therapeutic agent comprising the compound of the formula II labeled with a radioactive metal element, respectively.

DETAILED DESCRIPTION OF THE INVENTION

In the above formulae, n may be any integer of 2 to 10 (both inclusive), preferredly 2 to 8, and more preferredly 2 to 6. The group $C_nH_{2n}$ includes straight chain (i.e. polymethylene) groups and a branched chain (e.g. having one or more methyl side chains) groups.

In the above formula I, the group represented by A may be any monovalent group formed by reacting one of the two reactive groups of a cross linking regent. Preferred group A has a molecular weight of about 100 to about 1000 and/or has at least one physiologically cleavable linking group. In the more preferred group A, said physiologically cleavable linking group is selected from the group consisting of —O—, —COO—, —S—, —SS—, —SO— and —SO$_2$—.

Suitable examples of the group A includes:

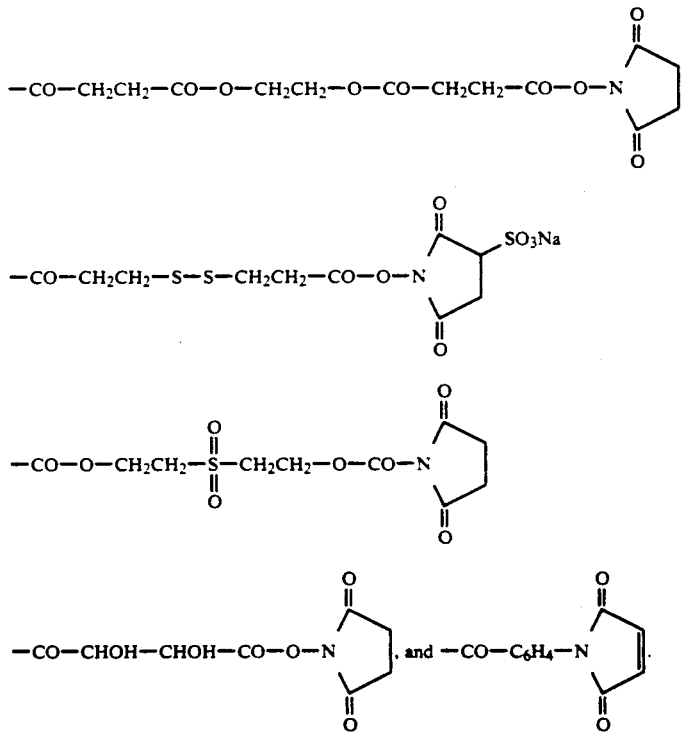

In the above formula II, the group represented by A' may be any bivalent group formed by reacting both the reactive groups of a cross linking reagent. Preferred group A' has a molecular weight of about 60 to about 900 and/or has at least one physiologically cleavable linking group. In the more preferred group A', said physiologically cleavable linking group is selected from the group consisting of —O—, —COO—, —S—, —SS—, —SO— and —SO$_2$—. Suitable examples of the group A' includes:

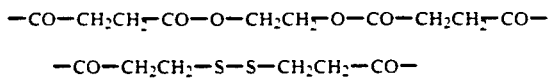

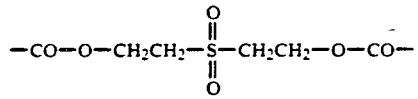

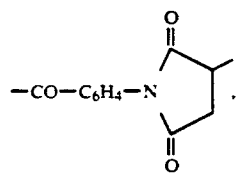

—CO—CHOH—CHOH—CO—, and

—CO—C₆H₄—N (succinimide ring)

The cross linking reagent referred to in the groups A and A' is intended to mean any compound having two or more reactive groups which may react with an amino group, a hydroxy group, a mercapt group, a dithio group, etc. to form a bond to N, O or S atom thereof, at least one of said reactive groups being capable of reacting with an amino group. Such reactive groups include active esters, such as succinimidyl ester, sulfosuccinimidyl ester, etc. imidoesters, nitroarylhalides (these being capable of reacting with an amino group), and disulfides, maleimides, thiophthalimides, active halogens (these being capable of reacting with a mercapt group), and so on. The preferred cross linking reagent contains at least one bond easily cleavable in vivo at the moiety other than the reactive groups, or has at least one bond formed by the reactive groups which is easily cleavable in vivo. Examples of such bond are —O—, —COO—, —S—, —SS—, —SO—, —SO$_2$—, etc.

A preferred group of the cross linking reagents is represented by the formula

X—Q—Y wherein X and Y are the same or different reactive groups, and Q is a carbon skeleton, with the proviso that Q contains at least one of O and S atoms in the basic skeleton, or where it does not contain the said atom in the basic skeleton, at least one of X and Y is a reactive group which forms a bond easily cleavable in vivo. The said carbonic skeleton contains 2 to 20, preferredly 3 to 16, more preferredly 4 to 12 carbon atoms, and may contain heteroatom(s) as a member of an heteroaromatic nucleus or in the form of a functional group such as a carbonyl.

Suitable examples of the bifunctional bridging reagent are as follows:
bis[2-(succinimidoxycarbonyloxy)ethyl]sulfone (BSOCOES),
disuccinimidyltartarate (DST),
3,3'-dithiobis(succinimidylpropionate) (DSP),
3,3'-dithiobis(sulfosuccinimidylpropionate) (DTSSP),
ethyleneglycolbis(succinimidylsuccinate) (EGS),
ethyleneglycolbis(sulfosuccinimidylsuccinate) (sulfo-EGS),
bis[2-(sulfosuccinimidoxycarbonyloxy)ethyl]sulfone (sulfoBSOCOES),
dimethyl-3,3'-dithiobispropionimidate.2HCl (DTBP),
dimethyladipimidate.2HCl (DMA),
dimethylpimelimidate.2HCl (DMP),
dimethylsuberimidate.2HCl (DMS),
m-maleimidobenzoylsulfosuccinimide ester (sulfoMBS),
N-succinimidyl-3-(2-pyridyldithio)propionate (SPDP),
2-iminothiolane.HCl,
bis(maleimido)methylether (BMME),
sulfosuccinimidyl-2-(m-azido-o-nitrobenzamido)ethyl-1,3'-dithiopropionate (SAND),
sulfosuccinimidyl-2-(p-azidosalicylamido)ethyl-1,3'-dithiobispropionate (SASD).

Particularly suitable examples of the cross linking reagent include the following compounds.

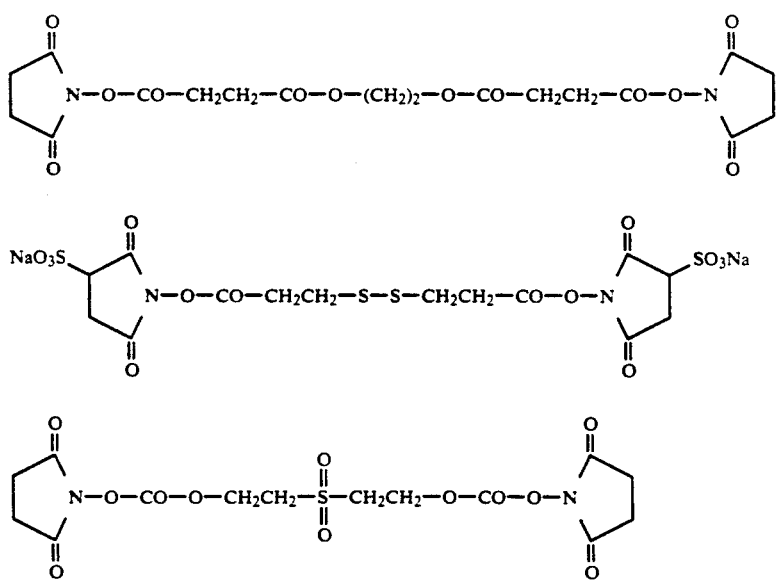

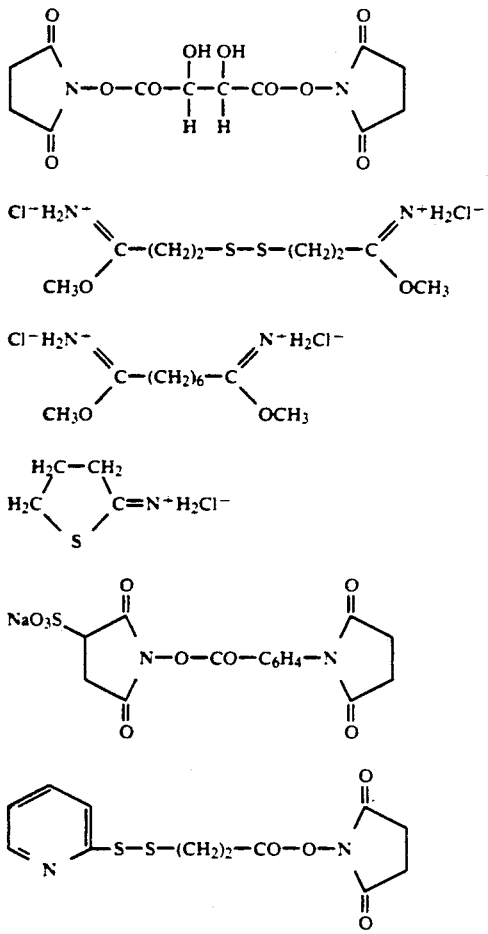

The term "polypeptide compound" represented by B refers to compounds having multiplicity of peptide bond formed by natural or unnatural amino acids and optionally one or more non-peptide moiety such as sugar, lipid or phosphoric ester and include both compounds known and unknown to have any particular physiolosical activity (e.g. therapeutic activity). Such compounds are polypeptides, simple proteins and conjugated proteins (lipoproteins and glycoproteins, etc.). The preferred polypeptide compounds include serum proteins (e.g. albumin, fibrinogen, etc.), enzymes (e.g. urokinase, streptokinase, TPA, etc.), peptide hormones (e.g. adrenal cortical hormone, thyroid stimulating hormone, insulin, etc.), antibodies (e.g. IgG, IgE, IgM, IgA, IgD and the fragments Fab, Fab', F(ab')$_2$, etc.), peptide antibiotics (e.g. bleomycin, etc.). Those exhibiting specific distribution, accumulation or behavior in vivo are preferred.

The radioisotope may be either metal or non-metal, but metal is preferred. Specific examples of the radioactive metal atom include diagnostic gamma-ray-emitting nuclide (e.g. $^{111}$In, $^{99m}$Tc, $^{67}$Ga, etc.), a diagnostic positron-emitting nuclide (e.g. $^{68}$Ga, $^{62}$Cu, $^{62}$Zn, etc.), a therapeutic beta-ray-emitting nuclide (e.g. $^{90}$Y, $^{186}$Re, $^{188}$Re, $^{153}$Sm, $^{212}$Pb, etc ) and a therapeutic alpha-ray-emitting nuclide (e.g. $^{211}$Bi, etc.).

Examples of physiologically acceptable salts of the compounds (I) and (II) include alkali metal salts such as sodium salts, potassium salts, etc., and ammonium salts.

The compounds of formula (I) can be obtained by reacting a DTPA amide derivative having the following formula

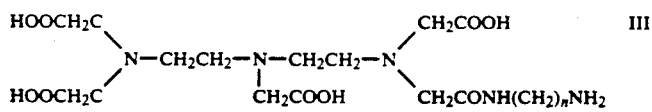

wherein n is an integer of 2 to 10 or a salt thereof with a cross linking reagent which will provide a group A thereto. Any of the above mentioned cross linking reagent can be used in this reaction. This reaction is carried out by combining a compound (III) and the cross linking reagent in an appropriate solvent such as a phosphate buffer and then stirring at a moderate temperature such as between cooling and slight heating, for example at room temperature for several tens minutes to a few hours, for example for 30–60 minutes. Usually the resultant compounds (I) are used without isolation for the preparation step of the compounds (II), but if particularly required, they may be isolated. Isolation is carried out by applying any combination of purification methods such as chromatography and a separation methods such as precipitation by addition of a non aqueous solvent. Preferred examples of the compounds (I) are as follows: (DTPAM- represents a DTPA monoalkylamide group of the formula:

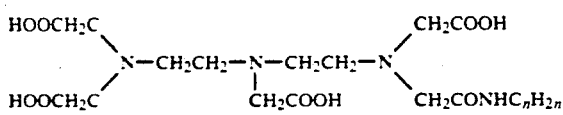

peptide synthesis. Among the acid halides, acid chloride is the most frequently used. Examples of the acid anhydrides include cyclic anhydrides and mixed anhydrides,

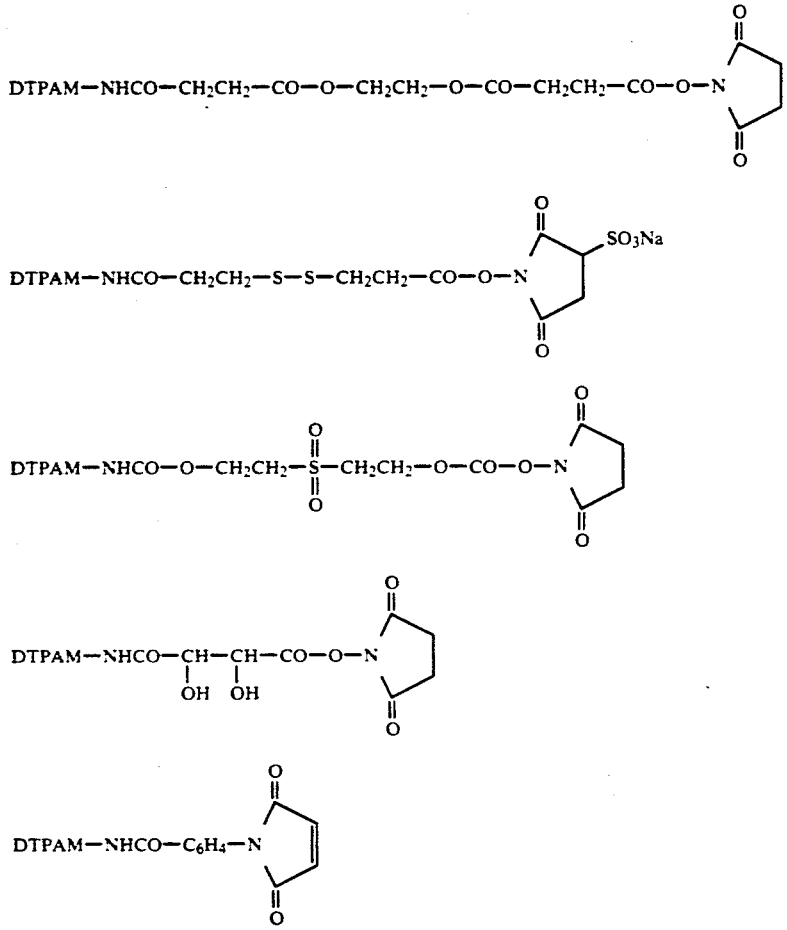

Among compounds of the formula III, those represented by the formula IIIa:

such as dialkylphosphoric acid mixed anhydride, dialkylphosphorous acid mixed hydride, alkylcarbonic acid

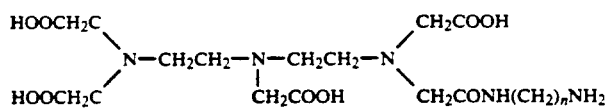    IIIa wherein n is an integer of 3 to 10, are novel.

The compounds (III) may be prepared by reacting DTPA or a reactive derivative at one or more carboxyl groups thereof (the remaining carboxyl groups may be protected by any carboxyl protecting groups conventionally used in the peptide synthesis) with diamine $H_2NC_nH_{2n}NH_2$ or a reactive derivative at one or more amino group thereof (the remaining amino group amy be protected by any amino protecting groups are present), subjecting the resultant product to removal reaction of the protecting group. DTPA is commercially available. Examples of the reactive derivatives at the carboxyl group of DTPA include acid halides, acid anhydries (including mixed acid anhydrides), active esters, active amides, etc., conventionally adopted for mixed anhydride aliphatic carboxylic acid (e.g. pivalic acid, trichloroacetic acid) mixed anhydride etc. with cyclic anhydrides being preferred. Examples of the activated esters include methyl ester, ethyl ester, cyanomethyl ester, p-nitrophenyl ester, an ester with N-hydroxysuccinimide etc. Examples of the activated amides include an amide with imidazole, dimethylimidazole or triazole. Examples of the reactive derivatives at the amino group of diamine are Schiff's bases with an aldehyde (e.g. acetaldehyde, isopentanal, benzaldehyde), a reaction product with a silyl compound (e.g. trimethylsilyl chloride, trimethylsilylacetamide), a reaction product with a phosphorus compound (e.g. phosphorus trichloride, phosphorus oxychloride) etc., conventionally adopted for peptide synthesis.

Examples of the protecting groups for residual carboxyl group of DTPA include those conventionally adopted in the peptide synthesis, such as phthalimido ester, succinimidomethyl ester pivaloyloxymethyl ester, benzyl ester or trimethylsilyl ester. Examples of the protecting groups for residual amino group of the compound (II) include those conventionally adopted in the peptide synthesis, such as benzyloxycarbonyl, t-butoxycarbonyl, benzyl, trityl, phthaloyl, trifluoroacetyl, trimethyl silyl etc.

Also, the reaction may be effected using DTPA as such, i.e. in the form of carboxylic acid, in the presence of a condensing agent conventionally used for peptide synthesis, such as $SOCl_2$, $SO_2Cl_2$, $PCl_3$, $PCl_5$, $POCl_3$, $PBr_3$, or N,N'-dicyclohexyl carbodiimide (DCC), N-cyclohexyl-N'-morpholinoethyl carbodiimide, N,N'-diisopropyl carbodiimide, $ClCO_2CH_3$, $ClCO_2C_2H_5$, $BrCO_2CH_3$, $(CH_3CO)_nO$, N-ethylbenzisoxazolium salts, 2-chloro-1-methylpyridinium salt, N,N'-carbonyl diimidazole (CDI), etc.

The reaction may be usually carried out in an inert solvent. Examples of the solvent include dioxane, methylene chloride, chloroform, ether, tetrahydrofuran (THF), acetone, dimethylformamide (DMF), dimethylsulfoxide (DMSO), pyridine, acetonitrile, benzene, toluene, xylene etc. In order to avoid the formation of by-product, it is desirable to limit the molarity of one of the compounds used in the reaction or to restrict the reaction conditions. The protecting groups are removed by any conventional removal method, for example hydrolysis, reduction, reaction with hydrazine or the like. The reaction product may be separated and recovered by any conventional methods such as concentration- crystallization, chromatography, etc. The compound (III) wherein $C_nH_{2n}$ is $CH_2CH_2$ is known, and may be prepared according to the known method [J. Med. Chem., 31, pp. 898-901 (1988)].

The compounds of formula (II) may be obtained by reacting a compound of formula (I) or its salt with a polypeptide compound which will provide a group B thereto. As the polypeptide compound, those illustrated above are used. This reaction is carried out by combining a compound (I) and a polypeptide compound in an appropriate solvent such as a phosphate buffer and then stirring at a moderate temperature such as between cooling and slight heating, for example at room temperature for several tens minutes to a few hours, for example for 30-60 minutes. Usually, the compounds (I) are used in situ, i.e. in the form contained in the reaction solution used for preparation thereof. After the reaction is completed, any unreacted reactive group in the cross linking agent is decomposed by an appropriate stopping (or quenching) agent such as ammonium acetate and then the desired compound (II) is separated and recovered by an appropriate separation methods such as chromatography.

The compounds (II) labeled with radioactive metal element are obtained by adding an aqueous solution of a water-soluble compound of radioactive metal to a solution of a compound (II). As the water-soluble compound of the radioactive metal, halide, for example, is used. Labeling is effected in the conventional manner.

The compounds (II) are useful as a carrier for a radioactive element. The compounds (II), which has four carboxyl groups in the part derived from DTPA, allowing thereby to capture metallic atoms, is suitable for labeling by different radioisotopes. The compounds (II) also provide an extremely high labeling efficiency. Therefore, the compounds (II) are useful as a carrier for a radioactive element.

On using as a carrier, the compounds (II) may be stored in the form of an aqueous solution, but are advantageously stored in the solid form as a lyophilisate. In the latter case, the compounds (II) are dissolved in a sterilized water, a physiological saline, a buffer, etc. prior to use. In addition, if required, an auxiliary solubilizing agent (e.g. an organic solvent), a pH controlling agent (e.g. an acid, a base, a buffer), a stabilizer, a preserving agent, an isotonizing agent, a reducing agent, an oxidizing agent (for maintaining the atomic valence), etc. may be added.

The compound (II) labeled with radioactive metal element may be used as a radioactive diagnostic agent by external measurement and quantitation of the radioactivity emitted therefrom. Further, in the radiotherapy for treating malignant neoplasm such as cancer, they may be used as a therapeutic agent. For these use, it is advantageous to choose, as the polypeptide moiety, such a compound as specifically accumulates at a particular organ or tissue of a diagnostic or therapeutic target. Such compounds include, for example, peptide hormones, antibodies and fragments thereof. For instance, anti-myocardial myosin antibody is used for diagnosing myocardial infarction. The amount of the radioactive metal is one that can afford information sufficient to diagnose, or one that can provide the desired therapeutic effect, but desirably one that can keep a radiation exposure of any other organs or tissues as low as possible. Administration is usually effected through an intravenous route, but depending upon the purpose, any other administration route may be employed.

Since the compounds (II) of the present invention have allowed the group A' provided by the cross linking reagent to intervene between the DTPA moiety and the polypeptide moiety, expansion of a range of application is realized by selecting an appropriate group to impart the compounds (II) any property suitable for the purpose. For instance, by including a group easily cleavable in vivo in the bridging reagent or by binding the bridging reagent using such a group, a blood clearance of the radioactive metal is promoted, which leads to decrease in undesired side effects. Also, by using a substance react in an aqueous solvent as the bridging reagent, the reaction under a mild condition is enabled and binding to a less stable polypeptide compound is facilitated.

Moreover, since the DTPA moiety and the terminal amine in the compounds (III) are joined via a fatty chain ($C_nH_{2n}$) an improved molecular flexibility and a better stability upon the radioactive metal binding thereto are provided, in comparison with those joined via an aromatic nucleus. In addition, they have various advantages such as rapider excretion, lesser antigenicity, easier purification, etc.

Additionally, by choosing suitably the compound in the polypeptide moiety, a specific distribution and an accumulation at a particular organ may be enabled. This advantage can not be seen in a known compound having a sugar such as inulin in place of peptide compound.

The compounds of the present invention are metabolized in vivo (e.g. in liver) into DTPA and rapidly (e.g. 90% within one hour) excreted into urine. Therefore, a retention time in vivo is extremely short and so that a period for exerting toxicity is short. For instance, when they were administered to an animal (a rat) at a dosage of 300 microgram/kg, no animal died and no abnormality was observed in behaviors during this experiment and in an autopsy. Since the above administered amount is about 20 times the estimated amount in clinical dosage, the above results indicate that the compounds of the present invention have extremely high safety.

The present invention is now illustrated in more detail by way of the following Examples.

In the Examples, % is given by weight %, unless otherwise defined. The following abbreviation are employed.

DTPA=diethylenetriaminepentaacetic acid;
hxnDTPA=N-[2-bis(carboxymethyl)aminoethyl]-N-[2-carboxymethyl-2-(6-aminohexyl)carbamoylmethyl]glycine [or diethylenetriaminepentaacetic acid mono(6-aminohexyl)-amide];
etnDTPA=N-[2-bis(carboxymethyl)aminoethyl]-N-[2-carboxymethyl-2-(2-aminoethyl)carbamoylmethyl]glycine [or diethylenetriaminepentaacetic acid mono(2-aminoethyl)-amide];
prnDTPA=N-[2-bis(carboxymethyl)aminoethyl]-N-[2-carboxymethyl-2-(3-aminopropyl)carbamoylmethyl]glycine [or diethylenetriaminepentaacetic acid mono(3-aminopropyl)amide];
DTSSP=3,3'-dithiobis(sulfosuccinimidylpropionate);
EGS=ethyleneglycolbis(succinimidylsuccinate);
AMFab=anti-myocardial myosin monoclonal antibody fragment.

EXAMPLE 1

Preparation of a derivative of diethylenetriaminepentaacetic acid (n=6: hxnDTPA)

Anhydride of DTPA (5.3 g, 14.8 mmol) was suspended in dimethylformamide (150 ml) (hereinafter referred to as solution A). To a solution of 6-[N-(t-butoxycarbonyl)-amino]hexylamine hydrochloride ¼ hydrate (1.5 g, 5.83 mmol) dissolved in dimethylformamide (50 ml) was added 5N aqueous NaOH (1.17 ml) (hereinafter referred to as solution B). The solution B was added dropwise to the solution A at room temperature under stirring over a period of 30 minutes and then allowed to react for another 30 minutes. The reaction solution became clear, and dimethylformamide was distilled off to give a syrupy residue. The syrupy residue was treated with 8 ml of water and then 6 ml of concentrated hydrochloric acid in order to hydrolyzed unreacted anhydride and remove the protecting group. Thereafter, hxnDTPA was fractionated by column chromatography using a cation exchange resin (S-Sepharose FF, H+ form). The resulting fraction was concentrated and acetone was concentrated and acetone was added thereto to give strongly hygroscopic white precipitates (yield: 1.3 g). This product was identified as hxnDTPA by the following analysis. TLC: stationary phase: silica gel, developing solvent: 10% aqueous solution of ammonium acetate/methanol=⅓, a single spot appeared at RF=0.33 by I$_2$ coloring and nynhydrin coloring. Analysis: C$_{20}$H$_{37}$O$_9$N$_5$.3HCl.2-H$_2$O.2[CH$_3$COCH$_3$]

|         | C      | H     | N     | Cl     |
|---------|--------|-------|-------|--------|
| Found:  | 42.1%  | 7.3%  | 9.1%  | 14.4%  |
| Calcd.: | 41.47% | 7.49% | 9.30% | 14.12% |

FD-Mass spectrum: The parent peak (hxnDTPA.H$^-$) was recognized at m/e=492.

$^{13}$C-NMR: measured in D$_2$O using an external standard method where a signal of dioxane was 67.4 ppm. The measurement modes employed were complete decoupling and off-resonance.

| Chemical shifts of detected peaks/ppm | Assignment (underline C-atom) |
|---|---|
| 173.80(s) | 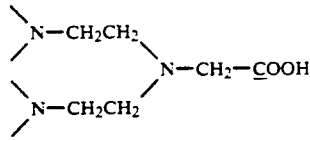 |
| 169.58(s) | —N—(CH$_2$COOH)$_2$ |
| 169.31(s) | —NHCOCH$_2$—N—CH$_2$COOH |
| 165.96(s) | —NHCOCH$_2$—N— |
| 56.95(t) | —NHCOCH$_2$—N— |
| 55.92(t) | —NHCOCH$_2$—N—CH$_2$COOH |
| 54.49(t) | 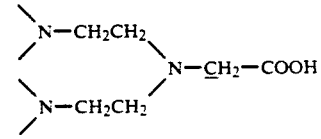 |
| 53.75(t) 50.19(t) | —N—(CH$_2$COOH)$_2$ H$_2$N—CH$_2$CH$_2$CH$_2$CH$_2$CH$_2$CH$_2$—NHCOCH$_2$— |
| 40.14(t) | 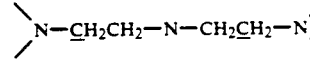 |
| 40.07(t) | 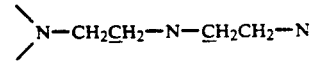 |
| 28.47(t) 27.17(t) 26.04(t) 25.75(t) | H$_2$N—CH$_2$CH$_2$CH$_2$CH$_2$CH$_2$CH$_2$—NHCOCH$_2$— |

The splitting mode of peak at measurement in the off-resonance mode is shown in parentheses.
s: singlet,
t: triplet

EXAMPLE 2

Preparation of a derivative of diethylenetriaminepentaacetic acid (n=3: prnDTPA)

Anhydride of DTPA (2.5 g, 7.0 mmol) was suspended in dimethylformamide (70 ml) (hereinafter referred to as solution A). To a solution of 2-[N-(t-butoxycarobonyl)-amino]propylamine hydrochloride ¼ hydrate (0.59 g, 2.74 mmol) dissolved in dimethylformamide (24 ml) was added 5N aqueous NaOH (0.55 ml) (hereinafter referred to as solution B). The solution B was added dropwise to the solution A at room temperature under stirring over a period of 30 minutes and then allowed to react for another 30 minutes. The reaction solution became clear, and dimethylformamide was distilled off to give a syrupy residue. The syrupy residue was treated with 3.8 ml of water and then 2.8 ml of concentrated hydrochloric acid in order to hydrolyze unreacted anhydride and remove the protecting group. Thereafter, prnDTPA was fractionated by column chromatography using a cation exchange resin (S-Sepharose FF, H+ form) The obtained fraction was concentrated and acetone was added thereto to give strongly hygroscopic white precipitates (yield;: 0.85 g). This product was identified as prnDTPA by the following analysis. FD-Mass spectrum: The parent peak (prnDTPA·H+) was recognized at m/e=450.

$^{13}$C-NMR: measured in D$_2$O using tetramethylsilylpropionic acid as an external standard.

| Chemical shifts of detected peaks | Assignment (underline C-atom) |
|---|---|
| 176.12 | 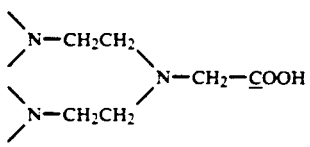 |
| 171.87 | —N$\pm$CH$_2$COOH)$_2$ |
| 171.76 | —NHCOCH$_2$—N—CH$_2$COOH |
| 169.03 | —NHCOCH$_2$—N— |
| 59.08 | —NHCOCH$_2$—N— |
| 58.35<br>58.16 | —N$\pm$CH$_2$COOH)$_2$ |
| 56.69 | —NHCOCH$_2$—N—CH$_2$COOH |
| 55.92 | 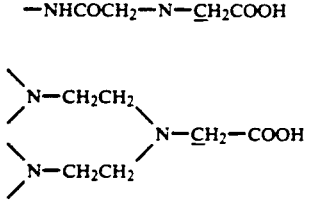 |
| 52.43<br>52.16 | H$_2$N—CH$_2$CH$_2$CH$_2$—NHCOCH$_2$—<br>H$_2$N—CH$_2$CH$_2$CH$_2$—NHCOCH$_2$— |
| 39.95 | >N—CH$_2$CH$_2$—N—CH$_2$CH$_2$—N< |
| 39.38 | >N—CH$_2$CH$_2$—N—CH$_2$CH$_2$—N< |

| Chemical shifts of detected peaks | Assignment (underline C-atom) |
|---|---|
| 29.25 | H$_2$N—CH$_2$CH$_2$CH$_2$—NHCOCH$_2$— |

EXAMPLE 3

Preparation of a derivative of diethylenetriaminepentaacetic acid (n=2: etnDTPA)

Anhydride of DTPA (2.5 g, 7.0 mmol) was suspended in dimethylformamide (70 ml) (hereinafter referred to as solution A). To a solution of 2-[N-(t-butoxycarbonyl)-amino]ethylamine hydrochloride ¼ hydrate (0.55 g, 2.74 mmol) dissolved in dimethylformamide (24 ml) was added 5N aqueous NaOH (0.55 ml) (hereinafter referred to as solution B). The solution B was added dropwise to the solution A at room temperature under stirring over a period of 30 minutes and then allowed to react for another 30 minutes. The reaction solution became clear, and dimethylformamide was distilled off to give a syrupy residue. The syrupy residue was treated with 3.8 ml of water and then 2.8 ml of concentrated hydrochloric acid in order to hydrolyze unreacted anhydride and remove the protecting group. Thereafter, etnDTPA was fractionated by column chromatography using a cation exchange resin (S-Sepharose FF, H+ form) The resultant fraction was concentrated and acetone was added thereto to give strongly hygroscopic white precipitates (yield: 0.85 g). This product was identified as etnDTPA by the following analysis.

TLC: stationary phase: silica gel, developing solvent: 10% aqueous solution of ammonium acetate/methanol=1/1, a single spot was observed at Rf=0.48 by I$_2$ coloring and nynhydrin coloring.

FD-Mass spectrum: the parent peak (etnDTPA·H+) was confirmed at m/e=436.

$^{13}$C-NMR: measured using the same method and mode as those of Example 1.

| Chemical shifts of detected peaks | Assignment (underline C-atom) |
|---|---|
| 173.81(s) | 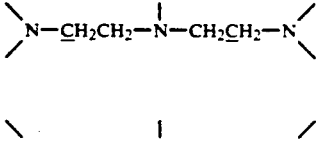 |
| 169.86(s) | —N$\pm$CH$_2$COOH)$_2$ |
| 169.75(s) | —NHCOCH$_2$—N—CH$_2$COOH |
| 167.97(s) | —NHCOCH$_2$—N— |
| 56.78(t) | —NHCOCH$_2$—N— |
| 55.93(t) | —NHCOCH$_2$—N—CH$_2$COOH |

-continued

| Chemical shifts of detected peaks | Assignment (underline C-atom) |
|---|---|
| 54.48(t) | ⟩N—CH$_2$CH$_2$⟨ ⟩N—$\underline{C}$H$_2$—COOH / ⟩N—CH$_2$CH$_2$/ |
| 53.57(t) | —N+$\underline{C}$H$_2$COOH)$_2$ |
| 53.49(t) | |
| 50.48(t) | H$_2$N—CH$_2$$\underline{C}$H$_2$—NHCOCH$_2$—N— |
| 50.21(t) | H$_2$N—$\underline{C}$H$_2$CH$_2$—NHCOCH$_2$—N— |
| 39.44(t) | ⟩N—$\underline{C}$H$_2$CH$_2$—N—CH$_2$$\underline{C}$H$_2$—N⟨ |
| 37.57(t) | ⟩N—CH$_2$$\underline{C}$H$_2$—N—$\underline{C}$H$_2$CH$_2$—N⟨ |

The splitting mode of a peak at measurement in the off-resonance mode is shown in parentheses.
s: singlet.
t: triplet

EXAMPLE 4

Preparation of EGS-hxnDTPA

To a solution of hxnDTPA hydrochloride in DMF (1×10$^{-4}$ mol/ml, 2 ml) was added 40 μl of 5N NaOH, then a solution of EGS in DMF (1×10$^{-4}$ mol/ml, 2 ml), and the resultant mixture was stirred at room temperature for 30 minutes. Thereafter, EGS-hxnDTPA was fractionated by column chromatography using TSK G-1000H (eluent: DMF). The solvent was distilled off from the obtained fraction, and acetone was added thereto to give strongly hygroscopic white precipitates.

EXAMPLE 5

Preparation of bovine IgG-(DTSSP)-hxnDTPA

To a neutral aqueous solution of hxnDTPA (2×10$^{-4}$ mol/ml, 50 μl) was added 0.2M phosphate buffer (pH 9.2, 200 μl), then a solution of DTSSP in 0.1M phosphate buffer (pH 7.5, 5.75×10$^{-5}$ mol/ml, 175 μl, 1.01×10$^{-5}$ mol), and the resultant mixture was stirred at room temperature for 30 seconds. This solution (110 μl) was added to a solution of bovine IgG in 0.05M phosphate buffered saline (pH 7.5, 15 mg/ml, 1.6 ml), and the resultant mixture was stirred at room temperature for 30 minutes. Then, 30 μl of 1M aqueous ammonium acetate was added thereto, and the mixture was stirred at room temperature for 10 minutes to decompose the unreacted DTSSP. A monomeric fraction was separated by gel chromatography using Sephacryl S-300SF [2.2 cm (column inside diameter)×75 cm (length), elution buffer: 0.2M citric acid (pH 5.8), elution rate: about 15.5 ml/h] to give the desired bovine IgG-(DTSSP)-hxnDTPA.

EXAMPLE 6

Preparation of bovine IgG-(EGS)-hxnDTPA

To a neutral aqueous solution of hxnDTPA (2×10$^{-4}$ mol/ml, 50 μl) was added 0.2M phosphate buffer (pH 9.2, 200 μl), then a solution of EGS in dimethylsulfoxide (1.01×10$^{-4}$ mol/ml, 120 μl, 1.3×10$^{-5}$ mol), and the mixture was stirred at room temperature for about one minute. This solution (50 μl) was added to a solution of bovine IgG in 0.05M phosphate buffered saline (pH 7.5, 15 mg/ml, 1.6 ml), and the resultant mixture was stirred at room temperature for one hour. Then, 30 μl of 1M aqueous ammonium acetate was added thereto, and the mixture was stirred at room temperature for 10 minutes to decompose the unreacted EGS. A monomeric fraction was separated by gel chromatography using Sephacryl S-300SF [2.2 cm (column inside diameter)×75 cm (length), elution buffer: 0.2M citric acid (pH 5.8), elution rate: about 16 ml/h] to give the desired bovine IgG-(EGS)-hxnDTPA.

EXAMPLE 7

Preparation of AMFab-(DTSSP)-hxnDTPA

To a neutral aqueous solution of hxnDTPA (2×10$^{-4}$ mol/ml, 60 μl) was added 0.2M phosphate buffer (pH 9.2, 0.42 ml), then a solution of DTSSP in 0.2M phosphate buffer (pH 9.2, 30.43 mg/ml, 0.12 ml), and the obtained mixture was stirred at 4° C. for 30 minutes. This solution (0.45 ml) was added to a mixture of a solution of AMFab in 0.05M phosphate buffer (pH7.8, 15 mg/1.5 ml) and 0.2M phosphate buffer (pH 9.2, 0.45 ml), and the mixture was stirred at 4° C. for three hours. Then, 0.1 ml of 1M aqueous ammonium acetate was added thereto and the mixture stirred at 4° C. for one hour to decompose the unreacted DTSSP. A monomeric fraction was separated by gel chromatography using Sephacryl S-200SF [2.2 cm (column inside diameter)×50 cm (length), elution buffer: 0.1M citric acid (pH 6), elution rate: about 15.5 ml/h] to give the desired AMFab-(DTSSP)-hxnDTPA.

EXAMPLE 8

Preparation of AMFab-(DTSSP)-etnDTPA

To a neutral aqueous solution of etnDTPA (1×10$^{-4}$ mol/ml, 87.5 μl) was added 0.2M phosphate buffer (pH 9.2, 263 μl), then a solution of DTSSP in 0.2M phosphate buffer (pH 9.2, 5×10$^{-5}$ mol/ml, 100 μl), and the mixture was stirred at 4° C. for 30 minutes. This resultant solution (180 μl) was added to a mixture of a solution of AMFab in 0.05M phosphate buffered saline (pH 7.8, 10.8 mg/ml, 0.58 ml) and 0.2M phosphate buffer (pH 9.2, 180 μl), and the resulting mixture was stirred at 4° C. for three hours. Then, 100 μl of 1M aqueous ammonium acetate was added thereto and the mixture was stirred at 4° C. for one hour to decompose the unreacted DTSSP. A monomeric fraction was separated by gel chromatography with TSKG-2000SM [0.75 cm (column inside diameter)×30 cm (length)+0.75 cm (guard column inside diameter)×7.5 cm (length), elution buffer: 0.1M citric acid (pH 6), elution rate: about 0.75 ml/min.] to give the desired AMFab-(DTSSP)-etnDTPA.

EXAMPLE 9

Preparation of bovine IgG-(DTSSP)-hxnDTPA-$^{111}$In and biodistribution in rats To a solution of bovine IgG-(DTSSP)-hxnDTPA (2.5 ml, corresponding to 1.56 mg of IgG) obtained according to the procedure of Example 5 was added a solution of $^{111}$InCl$_3$ (0.2 ml, 2 mCi/ml) to give the bovine IgG-(DTSSP)-hxn-DTPA-$^{111}$In. To examine the labeling efficiency, it was subjected to TLC using silica gel as a stationary phase and 10% aqueous CH$_3$COONH$_4$/CH$_3$OH=½ as a developing solvent, and scanning was carried out using a radiochromatoscanner. 99.5% of the radioactivity was detected at the origin, while the remaining 0.5% was observed near Rf=0.35 corresponding to $^{111}$In-hxnDTPA etc.

From the above results, it may be said that the bovine IgG-(DTSSP)-hxnDTPA-$^{111}$In prepared according to the above method has a labeling efficiency of 99.5%.

The bovine IgG-(DTSSP)-hxnDTPA-$^{111}$In prepared according to the above method was injected intravenously to several SD female rats (dose: 0.1 ml per animal, corresponding to about 58 μg of IgG, and to about 15 μCi as $^{111}$In), and the time course of the biodistribution with the lapse of time was investigated.

As the control, the same examination as above was carried out using $^{111}$In-labeled, bovine IgG-DTPA obtained by conventional DTPA anhydride method (a labeling efficiency of an administration sample was 97.3%).

The results are shown in the following Table. From the values shown in the Table, it is understood that, those employing DTSSP as spacer have a high renal accumulation, but exhibit a rapid blood clearance resulting rapid urinary excretion, and a low non-specific distribution in the remaining whole body (bone, muscle, skin, etc.). Further, their low hepatic accumulation clearly demonstrates an effect resulted by incorporation of —S—S— between the protein and chelate.

TABLE 1

| | Bovine IgG-(DTSSP)-hxnDTPA-$^{111}$In | | | |
|---|---|---|---|---|
| | Injected Dose/Organ (%) Time after administration (hours) | | | |
| Organs | 1 | 6 | 24 | 48 |
| Liver | 6.781 | 4.013 | 2.901 | 2.721 |
| Spleen | 0.398 | 0.167 | 0.111 | 0.143 |
| Kidneys | 4.758 | 17.66 | 15.47 | 13.61 |
| Heart | 0.701 | 0.291 | 0.051 | 0.029 |
| Lungs | 1.588 | 0.552 | 0.133 | 0.069 |
| Stomach | 0.300 | 0.170 | 0.057 | 0.045 |
| Small intestine | 4.086 | 5.724 | 0.536 | 0.366 |
| Large intestine | 0.833 | 6.172 | 4.451 | 0.717 |
| Urine | 7.901 | 36.73 | 58.05 | 59.59 |
| Feces | 0.000 | 0.107 | 10.78 | 17.88 |
| Carcass | 28.62 | 17.77 | 6.278 | 4.431 |
| Whole blood | 71.23 | 18.75 | 2.026 | 0.712 |

The total amount of blood is calculated as 6.4% based on a body weight of rat.

TABLE 2

| | Bovine IgG-DTPA-$^{111}$In | | | |
|---|---|---|---|---|
| | Injected Dose/Organ (%) Time after administration (hours) | | | |
| Organs | 1 | 6 | 24 | 48 |
| Liver | 7.904 | 8.031 | 9.152 | 10.85 |
| Spleen | 0.498 | 0.455 | 0.458 | 0.574 |
| Kidneys | 1.373 | 1.943 | 3.217 | 4.531 |
| Heart | 0.882 | 0.835 | 0.544 | 0.418 |
| Lungs | 2.446 | 1.783 | 1.132 | 0.860 |
| Stomach | 0.332 | 0.414 | 0.457 | 0.369 |
| Small intestine | 2.786 | 4.117 | 3.003 | 2.287 |
| Large intestine | 0.620 | 2.800 | 4.032 | 2.222 |
| Urine | 2.653 | 3.255 | 4.603 | 7.744 |
| Feces | 0.000 | 0.001 | 2.889 | 7.037 |
| Carcass | 26.19 | 36.61 | 50.56 | 50.24 |
| Whole blood | 97.90 | 73.25 | 35.75 | 21.73 |

The total amount of blood is calculated as 6.4% based on a body weight of rat.

EXAMPLE 10

Preparation of bovine IgG-(EGS)-hxnDTPA-$^{111}$In and biodistribution in rats

To a solution of bovine IgG-(EGS)-hxnDTPA (2.5 ml, corresponding to 2.1 mg of IgG) obtained according to the procedure of Example 6 was added a solution of $^{111}$InCl$_3$ (0.2 ml, 2 mCi/ml) to give the bovine IgG-(EGS)-hxnDTPA-$^{111}$In.

In order to examine the labeling efficiency, it was subjected to TLC according to the method of Example 9. As a result, 99.7% of the radioactivity was present at the origin, while the remaining 0.3% was observed near Rf=0.35 corresponding to $^{111}$In-hxnDPTA etc. Therefore, it may be said that the labeling efficiency was 99.7%.

The bovine IgG-(EGS)-hxnDTPA-$^{111}$In prepared by the above method was used to investigate the time course of the biodistribution in rats with the elapse of time according to the method of Example 9.

The results are shown in the following Table. From the values shown in the Table, it is understood that adoption of EGS as a spacer (i.e. incorporating an ester bond between the protein and chelate) results in acceleration of blood clearance and thus promotion of urinary excretion. It may be said that, at the same time, an effect of reducing accumulation in liver and the remaining whole body was obtained.

TABLE 3

| | Bovine IgG-(EGS)-hxnDTPA-$^{111}$In | | | |
|---|---|---|---|---|
| | Injected Dose/Organ (%) Time after administration (hours) | | | |
| Organs | 1 | 6 | 24 | 48 |
| Liver | 6.942 | 5.491 | 4.699 | 4.587 |
| Spleen | 0.445 | 0.304 | 0.229 | 0.245 |
| Kidneys | 1.125 | 1.448 | 1.582 | 1.919 |
| Heart | 0.693 | 0.753 | 0.313 | 0.147 |
| Lungs | 1.909 | 1.401 | 0.636 | 0.352 |
| Stomach | 0.266 | 0.322 | 0.259 | 0.142 |
| Small intestine | 3.032 | 4.480 | 2.015 | 1.228 |
| Large intestine | 0.514 | 5.136 | 5.546 | 2.408 |
| Urine | 5.303 | 21.03 | 39.80 | 49.81 |
| Feces | 0.000 | 0.001 | 8.065 | 16.68 |
| Carcass | 25.46 | 29.14 | 25.33 | 17.75 |
| Whole blood | 89.48 | 56.08 | 19.98 | 8.057 |

The total amount of blood is calculated as 6.4% based on a body weight of rat.

TABLE 4

Bovine IgG-DTPA-$^{111}$In

| Organs | Injected Dose/Organ (%) Time after administration (hours) | | | |
|---|---|---|---|---|
| | 1 | 6 | 24 | 48 |
| Liver | 7.904 | 8.031 | 9.152 | 10.85 |
| Spleen | 0.498 | 0.455 | 0.458 | 0.574 |
| Kidneys | 1.373 | 1.943 | 3.217 | 4.531 |
| Heart | 0.882 | 0.835 | 0.544 | 0.418 |
| Lungs | 2.446 | 1.783 | 1.132 | 0.860 |
| Stomach | 0.332 | 0.414 | 0.457 | 0.369 |
| Small intestine | 2.789 | 4.117 | 3.003 | 2.287 |
| Large intestine | 0.620 | 2.800 | 4.032 | 2.222 |
| Urine | 2.653 | 3.255 | 4.603 | 7.744 |
| Feces | 0.000 | 0.001 | 2.889 | 7.037 |
| Carcass | 26.19 | 36.61 | 50.56 | 50.24 |
| Whole blood | 97.90 | 73.25 | 35.75 | 21.73 |

The total amount of blood is calculated as 6.4% based on a body weight of rat.

EXAMPLE 11

Preparation of AMFab-(DTSSP)-hxnDTPA-$^{111}$In

To a solution of AMFab-(DTSSP)-hxnDTPA (1 ml, corresponding to 0.5 mg of Fab) obtained by the method of Example 7 was added a solution of $^{111}$InCl$_3$ (1 ml, 2 mCi/ml) to prepare AMFab-(DTSSP)-hxnDTPA-$^{111}$In.

In order to examine the labeling efficiency, it was subjected to TLC using silica gel as a stationary phase and 10% CH$_3$COONH$_4$/MeOH=1/1 as a developing solvent, and scanning was carried out using radiochromato-scanner. 98.7% of the radioactivity was present at the origin, while the remaining 1.3% was detected near Rf=0.5 corresponding to $^{111}$In-hxnDTPA etc. Therefore, it may be said that AMFab-(DTSSP)-hxnDTPA-$^{111}$In prepared by the above method has a labeling efficiency of 98.7%.

AMFab-(DTSSP)-hxnDTPA-$^{111}$In prepared by the above method was measured for its affinity constant by a radioimmunometric assay using major myocardial myosin as an antigen giving superior result of $Ka=1.5\times10^8 M^{-1}$ as compared with $Ka=1.0\times10^8 M^{-1}$ for an antibody prepared by a conventionally adopted anhydrous DTPA method.

EXAMPLE 12

Preparation of AMFab-(DTSSP)-etnDTPA-$^{111}$In

To a solution of AMFab-(DTSSP)-etnDTPA (1 ml, corresponding to 0.5 mg of Fab) obtained by the method of Example 8 was added a solution of $^{111}$InCl$_3$ (1 ml, 2 mCi/ml) to give AMFab-(DTSSP)-etnDTPA-$^{111}$In In order to examine the labeling efficiency, TLC was effected according to the method of Example 9. As the result, 98.2% of the radioactivity was present at the original point, while the remaining 1.8% was detected near Rf 0.5 corresponding to $^{111}$In-etnDTPA etc. Therefore, it may be said that AMFab-(DTSSP)-etnDTPA-$^{111}$In prepared by the above method has a labeling efficiency of 98.2%.

In a manner similar to Example 11, an affinity constant of AMFab-(DTSSP)-etnDTPA-$^{111}$In was measured and also a satisfactory result of $Ka=1.8\times10^8 M^{-1}$ was obtained.

EXAMPLE 13

The removal efficiency of unreacted bifunctional ligand(s)

AMFab-(DTSSP)-hxnDTPA and AMFab-(DTSSP)-etnDTPA prepared in Examples 7 and 8 respectively were estimated for the removal efficiency of unreacted free bifunctional ligand(s) after the reaction. As a control, an anhydrous DTPA conventionally adopted as a bifunctional ligand was used. A purification procedure used was a high performance liquid chromatography presently regarded as the most efficient one (column: TSK G-2000SW and TSK G-3000SW, elution rate 0.75 ml/min.). The results are shown in the following Table.

TABLE 5

Column: TSK G-2000SW

| Mode of binding | Eluting buffer | |
|---|---|---|
| | citric acid | 0.1M citric acid in saline |
| CA-DTPA | 17.7% | 17.5% |
| AMFab-(DTSSP) hxnDTPA | 2.3% | — |
| AMFab-(DTSSP) etnDTPA | 1.8% | — |
| CA-DTPA | 15.2% | 15.4% |
| AMFab-(DTSSP) hxnDTPA | — | — |
| AMFab-(DTSSP) etnDTPA | — | — |

1) The above % indicates a rate of peak shown by free ligand-$^{111}$In when the isolated monomeric fraction was labelled with $^{111}$In.
2) All the above eluting buffers have a pH of 6.

From the results shown in the above Table, it is understood that the purification efficiency obtained by the method of this invention is much higher than that by any conventional method, and therefore any other purification method is not required to be used jointly It may be said that this provides an excellent economical advantage.

EXAMPLE 14

Preparation of AMFab-(DTSSP)-prnDTPA

To a neutral aqueous solution of prnDTPA ($1\times10^4$ mol/ml, 36.6 µl) was added 0.2M phosphate buffer (pH 9.2, 163.4 µl) and then a solution of DTSSP in 0.2M phosphate buffer (pH 9.2; $2.09\times10^{-5}$ mol/ml, 100 µl), and the resultant mixture was stirred at 4° C. for 30 minutes. To this solution was added a solution of AMFab in 0.05M phosphate buffer saline (pH 7.8; 10.8 mg/ml, 500 µl) and the mixture was stirred at 4° C. for three hours. Then, 50 µl of 1M aqueous ammonium acetate was added thereto and the mixture was stirred at 4° C. for one hour to decompose unreacted DTSSP. Then, gel column chromatography using TSKG-2000SW [0.75 cm (column inside diameter)×30 cm (length)+0.75 cm (guard column inside diameter)+7.5 cm (length), elution buffer: 0.1M citrate buffer (pH 6), elution rate: 0.75 ml/min.] was effected to separate a monomeric fraction, which gave the AMFab-(DTSSP)-prnDTPA.

EXAMPLE 15

Preparation of AMFab-(DTSSP)-prnDTPA-$^{111}$In and biodistribution and excretion in rats To a solution of AMFab-(DTSSP)-prnDTPA (1 ml, corresponding to 0.5 mg as Fab) obtained according to the procedure of Example 14.was added a solution of $^{111}$InCl$_3$ (1 ml, 2 mCi/ml) to give AMFab-(DTSSP)-prnDTPA-$^{111}$In. In order to examine the labeling efficiency, it was subjected to TLC using silica gel as a stationary phase and 10% aqueous CH$_3$COONH$_4$/CH$_3$OH=1/1 as a developing solvent, and scanning was carried out using a radiochromato-scanner. 97.6% of the radioactivity emitted was detected at the origin, while the remaining 2.4% was observed near Rf 0.45 corresponding to prnDTPA-$^{111}$In etc. Therefore, it may be said that AMFab-(DTSSP)-prnDTPA-$^{111}$In prepared by the above method has a labeling efficiency of 97.6%.

The AMFab-(DTSSP)-prnDTPA-$^{111}$In prepared according to the above method was injected intravenously to several SD female rats (dose: 0.1 ml per animal, corresponding to about 25 μg as Fab, and to about 100 μCi as $^{111}$In), and the time course of the biodistribution was investigated. Also, at 3 hours after injection, a portion of urine was analyzed by HPLC [column: TSK G-2000SW, 0.75 cm (column inside diameter)×30 cm (length)+0.75 cm (guard column inside diameter)×7.5 cm (length), elution buffer: 0.1M phosphate buffer (pH 7) containing 0.1% polyethyleneglycol, elution rate: 0.75 ml/min, detector: a sigle channel analyzer (gamma-ray of 171 keV, 245 KeV detectable)] to examine metabolites in urine.

For the control, the same examination as above was carried out using $^{111}$In-labeled, AMFab-DTPA obtained by conventional DTPA anhydride method (a labeling efficiency of an administration sample was 85.8%).

The results are shown in the following Table. From the values shown in the Table, it may be said that, there are few apparent differences in the biodistribution for two reasons, i.e. for one reason that the labeling efficiency of AMFab-DTPA-$^{111}$In employed as a control is low (in the preparation of AMFab-DTPA, unreacted free DTPA is difficult to be removed, so that free DTPA-$^{111}$In would remain contained as much as 14.2%. Once free DTPA-$^{111}$In is administered, it rapidly disappears from blood to be excreted into urine.) and the other reason that AMFab per se, which has only a small molecular weight (about 50,000), tends to be subjected to excretion by glomerular filtration (difficult to be resorbed in tubulus) in rats. However, the results of HPLC urinalysis for three hours after administration indicate that, in case DTSSP was adopted as, a spacer, although only a few % of free prnDTPA-$^{111}$In is contained in the administration samples, the radioactive components derived from molecules with low molecular weight was detected no less than 48.3% in urine (the remaining 51.7% was those excreted in the form of Fab-(DTSSP)-prnDTPA-$^{111}$In, for which the molecular weight of Fab was small as mentioned above). This occurred because the spacer part was subjected to any metabolisis to liberate the prnDTPA-$^{111}$In moiety followed by excretion into urine. In case Fab-DTPA-$^{111}$In as a control substance was injected to rats, only the low molecular radioactive components whose amount corresponded to that of free DTPA-$^{111}$In contained in the administration sample were detected in urine, and it was confirmed that, for Fab-DTPA prepared by the conventional DTPA anhydride method, the bondage between protein and chelate was too strong to be metabolized in vivo. Thus, the analysis of urinary excretion clearly demonstrated an effect of incorporation of —S—S— between protein and chelate.

TABLE 6

AMFab-DTSSP-prnDTPA-$^{111}$In

| Organs | Injected Dose/Organ (%) Time after administration (hours) | | |
|---|---|---|---|
| | 1 | 3 | 6 |
| Liver | 4.74 | 3.81 | 3.26 |
| Spleen | 0.32 | 0.20 | 0.17 |
| Kidneys | 6.95 | 8.51 | 19.38 |
| Heart | 0.53 | 0.26 | 0.14 |
| Lungs | 1.79 | 1.36 | 0.51 |
| Stomach | 0.32 | 0.29 | 0.16 |
| Small intestine | 2.08 | 2.13 | 0.86 |
| Large intestine | 0.75 | 0.69 | 2.82 |
| Urine | 33.80 | 54.04 | 58.11 |
| Feces | — | — | 0.05 |
| Carcass | 25.67 | 17.41 | 9.12 |
| Whole blood* | 39.27 | 15.89 | 6.29 |

*The total amount of blood was calculated as 6.4% based on the body weight of rat.

TABLE 7

AMFab-DTPA-$^{111}$In*

| Organs | Injected Dose/Organ (%) Time after administration (hours) | | |
|---|---|---|---|
| | 1 | 3 | 6 |
| Liver | 3.96 | 3.54 | 3.53 |
| Spleen | 0.27 | 0.21 | 0.17 |
| Kidneys | 10.80 | 11.69 | 12.63 |
| Heart | 0.57 | 0.31 | 0.13 |
| Lungs | 1.56 | 0.99 | 0.51 |
| Stomach | 0.24 | 0.22 | 0.20 |
| Small intestine | 2.08 | 1.95 | 1.57 |
| Large intestine | 0.49 | 1.73 | 4.31 |
| Urine | 37.86 | 49.75 | 58.89 |
| Feces | — | — | — |
| Carcass | 23.55 | 23.70 | 15.55 |
| Whole blood* | 31.38 | 12.35 | 4.31 |

*The total amount of blood was calculated as 6.4% based on the body weight of rat.

TABLE 8

Urinalysis in rat receiving AMFab-(DTSSP)-prnDTPA-$^{111}$In and AMFab-DTPA-$^{111}$In (3 hours after administration).

| Sample | Retention time (min.)/Relative ratio % (Ratio against injected dose (% ID)*) | |
|---|---|---|
| AMFab-(DTSSP)- prnDTPA-$^{111}$In | 13.48/51.7% (27.9% ID) | 18.08/48.3% (26.1% ID) |
| AMFab-DTPA-$^{111}$In | 13.47/72.8% (36.2% ID) | 16.80/27.2% (13.5% ID) |

*Calculated values based on the urinary excretion at 3 hr postinjection shown in Tables 5 and 6, i.e., AMFab-(DTSSP)-prnDTPA-$^{111}$In: 54.04% and AMFab-DTPA-$^{111}$In: 49.75%.

EXAMPLE 16

Preparation of EGS-prnDTPA

An aqueous solution of prnDTPA.hydrochloride (1×10$^{-4}$ mol/ml) was neutralized by adding 40 μl of 5M NaOH and then lyophilized. The produced white solid was solubilized by adding 2 ml of DMF, and a solution of EGS in DMF (1×10$^{-4}$ mol/ml, 2 ml) was added. The mixture was stirred at room temperature for 30 minutes. Thereafter, gel column chromatography using TSKG-2000HxL [0.75 cm (column inside diameter)×30 cm (length)+0.6 cm (guard column inside diameter)×4 cm (length), eluent: DMF elution rate: 0.5 ml/min., sample loading amount: each time 500 μl] was effected to fractionate EGS-prnDTPA. The resultant fraction was concentrated by distilling off the solvent and acetone was added to give strongly hygroscopic white precipitates.

What is claimed is:

1. A compound of the formula II:

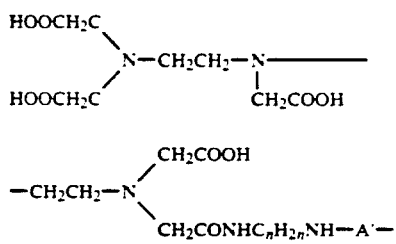

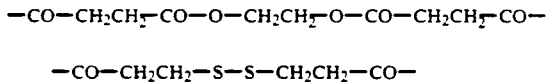

wherein n is an integer of 2 to 10,
A' is a bivalent linking group formed by reacting both the reactive groups of a cross linking reagent, and
A' is a residue of a polypeptide compound which exhibits specificity for a particular antigen or receptor, and physiologically acceptable salts of said compound.

2. The compound according to claim 1, wherein n is an integer of 2 to 6.

3. The compound according to claim 1, wherein A' has a molecular weight of about 100 to 1000.

4. The compound according to claim 1, wherein A' has at least one physiologically cleavable linking group.

5. The compound according to claim 4, wherein said physiologically cleavable linking group is selected from the group consisting of —O—, —COO—, —S—, —SS—, —SO— and —SO$_2$—.

6. The compound according to claim 5, wherein A' is selected from the group consisting of

—CO—CH$_2$CH$_2$—CO—O—CH$_2$CH$_2$—O—CO—CH$_2$CH$_2$—CO—

—CO—CH$_2$CH$_2$—S—S—CH$_2$CH$_2$—CO—

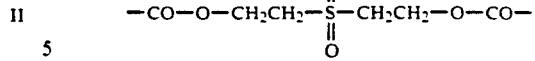

—CO—CHOH—CHOH—CO—, and

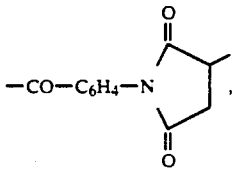

7. The compound according to claim 1, wherein B is selected from the group consisting of polypeptides, simple proteins, lipoproteins and glycoproteins.

8. The compound according to claim 1, wherein B is a protein having biological activity.

9. The compound according to claim 1, wherein B is selected from the group consisting of serum proteins, enzymes, peptide hormones, peptide antibiotics, antibodies and fragments thereof.

10. The compound according to claim 9, wherein said serum proteins are immunoglobulins.

11. A carrier for radioisotopes comprising at least one compound according to claim 1.

12. A radioactive diagnostic agent comprising the compound according to claim 1 labeled with a radioactive metal element.

13. The agent according to claim 12, wherein said radioactive metal element is selected from the group consisting of $^{111}$In, $^{99m}$Tc, $^{67}$Ga, $^{68}$Ga, $^{62}$Cu and $^{62}$Zn.

14. A radioactive therapeutic agent comprising the compound according to claim 1 labeled with a radioactive metal element.

15. The agent according to claim 14, wherein said radioactive metal element is selected from the group consisting of $^{90}$Y, $^{186}$Re, $^{188}$Re, $^{153}$Sm, $^{212}$Pb and $^{211}$Bi.

* * * * *

UNITED STATES PATENT AND TRADEMARK OFFICE
CERTIFICATE OF CORRECTION

PATENT NO. : 5,094,950

DATED : March 10, 1992

INVENTOR(S) : SUSUMU KONDO, ET AL

It is certified that error appears in the above-identified patent and that said Letters Patent is hereby corrected as shown below:

Claim 1 (column 25, line 17), change "A'" to --B--.

Signed and Sealed this

Thirteenth Day of April, 1993

Attest:

STEPHEN G. KUNIN

*Attesting Officer*      Acting Commissioner of Patents and Trademarks